United States Patent [19]

Arny et al.

[11] 4,161,084

[45] * Jul. 17, 1979

[54] METHOD FOR REDUCING TEMPERATURE AT WHICH PLANTS FREEZE

[75] Inventors: Deane C. Arny, Madison, Wis.; Steven E. Lindow, Berkeley, Calif.

[73] Assignee: Wisconsin Alumni Research Foundation, Madison, Wis.

[*] Notice: The portion of the term of this patent subsequent to Sep. 6, 1994, has been disclaimed.

[21] Appl. No.: 921,800

[22] Filed: Jul. 3, 1978

[51] Int. Cl.² .............................................. A01G 1/00
[52] U.S. Cl. ............................................ 47/2; 47/58; 424/93

[58] Field of Search ........................................ 47/2, 58

[56] References Cited

U.S. PATENT DOCUMENTS 4,045,910 9/1977 Arny et al. ................................. 47/2

Primary Examiner—Robert E. Bagwill
Attorney, Agent, or Firm—McDougall, Hersh & Scott

[57] ABSTRACT

The method for reducing the temperature at which freezing takes place in plants to reduce frost damage by the addition of non-ice nucleating bacteria to the plants prior to the onset of freezing temperature and preferably while the plants are in their seedling stage.

11 Claims, 1 Drawing Figure

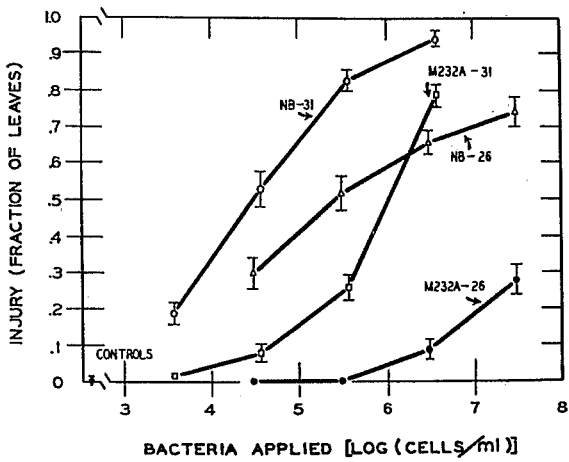

Figure  Frost damage to M232A pretreated corn seedlings challenged with different cell densities of E. herbicola or P. syringae. Corn seedlings were sprayed 3 days prior to freezing at -4.5 C with $3 \times 10^8$ cells/ml M232A in nutrient broth (● and ▫) or with nutrient broth alone (O and △) and were placed in a mist chamber. Two days prior to freezing plants were sprayed with different cell densities (shown on the abscissa) of P. syringae isolate #31 (▫ and O) or E. herbicola isolate #26 (● and △) in phosphate buffer and were returned to the mist chamber. Vertical bars represent the standard error of the determination of the mean.

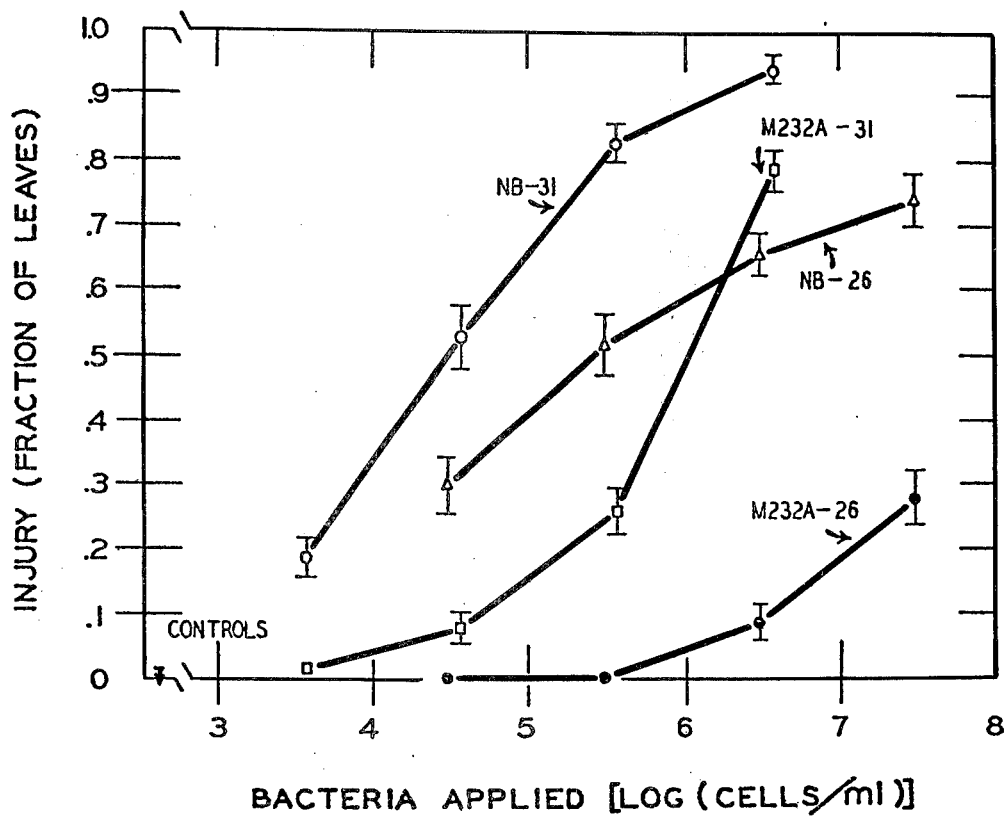

Figure   Frost damage to M232A pretreated corn seedlings challenged with different cell densities of E. herbicola or P. syringae. Corn seedlings were sprayed 3 days prior to freezing at -4.5 C with $3 \times 10^8$ cells/ml M232A in nutrient broth (● and ■) or with nutrient broth alone (O and △) and were placed in a mist chamber. Two days prior to freezing plants were sprayed with different cell densities (shown on the abscissa) of P. syringae isolate #31 (□ and O) or E. herbicola isolate #26 (● and △) in phosphate buffer and were returned to the mist chamber. Vertical bars represent the standard error of the determination of the mean.

METHOD FOR REDUCING TEMPERATURE AT WHICH PLANTS FREEZE

This invention relates to the protection of plants against frost injury.

Freezing and frost are major hazards in agricultural production in many parts of the world. Average losses in various agricultural crops in the United States alone, due to cold weather, have been estimated to vary from 8% for citrus fruits and apples to 30-40% for strawberries. It is estimated that within the United States, during the period of 1963-1968, an annual average of 3.6 million acres of cropland was destroyed by frost and that this lost production was valued at about 341 million dollars per year. More recent estimates place the losses due to frost damage at about 1.1 billion dollars per year.

Frost damage to growing tender plants is the result of ice formation in the plant cells. When ice forms in such plant cells, it tends rapidly to spread throughout the plant, causing irreparable damage, most notably to cell membrane continuity.

Since ice formation within the cells of such plants is invariably damaging, control from damage has been restricted in the prior art to physical methods which might prevent freezing of the plant tissues. Use has been made of artificial fogs, such as mist and smoke, the reduce radiative cooling of the plants and surrounding air. Portable heaters have been placed throughout the crop and crops have been covered with a form like material to prevent radiative and convective cooling and to capture heat radiated by the soil surface. Wind machines have been used to mix the cool surface layer air with the warmer upper level air with a view towards warming the entire lower air mass. Water has been applied by spray to the surfaces of the plants during the period of freezing temperature, utilizing the latent heat of fusion released by the freezing water to maintain the ice-water mixture at 0° C. as long as free water remains available to freeze.

These are all measures that require a considerable amount of equipment, and are operated at considerable expense, and consumption of energy.

In addition to such physical methods, use has been made of various chemical compounds applied to plants prior to freezing with a view towards lowering the temperature at which freezing would occur. Again, this is an expensive and temporary procedure which introduces problems of contamination and environmental damage.

None of the described procedures takes into account what we have discovered to be the fundamental mechanism of frost damage, i.e. at temperatures of $-8°$ to $0°$ C. It is an object of this invention to provide a method and means for protection of plants against injury by frost or freezing within the aforementioned temperature range, and it is a related object to provide a method of the type described wherein such protection can be applied prior to the onset of frost or freezing temperature, and preferably at a very early stage of plant growth, wherein such protection lasts over an extended period of time, sometimes throughout the life of the plant, in which such means for protection can be easily applied with readily available equipment, which is sufficiently universal for use to prevent frost and freezing injury with a wide variety of plants, and in which such treatment is relatively free of environmental contamination problems or problems with respect to contamination of the plants.

In our earlier issued U.S. Pat. No. 4,045,910, description is made of our discovery that treatment of plants with a bacterium identified as *Erwinia herbicola* var. ananus (M232A), before the onset of freezing temperature, was effective to protect the plant against frost damage.

Our continued research has established that there are hundreds of bacteria and other microorganisms normally present on agricultural plants, some of which have ice nucleating activity and others of which are non-ice nucleating.

We have found that protection of plants against frost damage is not exclusively dependent upon treatment of the plants with any particular bacterium, such as M232A, as described in our previously issued patent. Instead, our investigations have established that protection of plants against frost damage can be achieved by increasing the ratio on the plant of non-ice nucleating bacteria over the bacteria having ice nucleating activity over and above the ratio normally present on the plant, thereby reducing the number of ice nucleating active bacteria since the total number of bacteria on the leaves remained unchanged. Based upon this criteria, it will be seen that protection of plants against frost damage can be achieved by means other than physical or chemical means.

The desired change to increase the proportion of non-ice nucleating bacteria to ice nucleating bacteria on the plant can be accomplished in a number of ways. Non-ice nucleating bacteria, which have been isolated from the plant or other plants or derived from various collections, can be applied to the plants prior to onset of freezing temperature. However, it is desirable to make such additions as early in the plant life as possible. This concept is based upon the finding that the addition of ice nucleating bacteria, while the general population of bacteria on the plant is low, requires the addition of less non-ice nucleating bacteria to achieve a desired shift in the proportion between non-ice nucleating bacteria to ice nucleating bacteria. It is also based on the finding that, the sites for growth are more available for occupation by the applied non-ice nucleating bacteria thereby to block sites which may be occupied by ice nucleating bacteria for growth, thereby to minimize the growth of ice nucleating bacteria while the population of non-ice nucleating bacteria continues to increase. Thus, an important concept of the invention resides in the increase in the ratio of non-ice nucleating bacteria as compared to the ice nucleating bacteria normally on the plant by application of non-ice nucleating bacteria to the plant, preferably in early growth stages.

As used herein, the term "bacteria" is intended to include various microorganisms that populate plants and which increase in population during plant growth. As previously pointed out, literally hundreds of bacteria and other microorganisms exist on the plants, some of which are non-ice nucleating and others of which are ice nucleating. It would be impractical to attempt to identify one from the other by name since, even within a particular genus, some of the species within the genus will be ice nucleating while others are non-ice nucleating. Even within a species, some isolates will be non-ice nucleating and other isolates will ice nucleate. For example, within the species *P. syringae,* some 81 strains have been isolated which are ice nucleating and 4 strains have been isolated which are non-ice nucleating.

Within *E. herbicola*, some 41 isolates were ice nucleating while 4 were non-ice nucleating. On the other hand, within the species *P. tabaci*, 3 isolates have been found to be non-ice nucleating while no isolates have been discovered which are ice nucleating. The same applies with the species *E. stewartii* and *Corynebacterium nebraskensis* where 4 isolates tested were non-ice nucleating while no isolates tested were ice nucleating.

As a result, instead of seeking to identify the ice nucleating and non-ice nucleating bacteria or other microorganisms by name, the more appropriate manner for identification of bacteria for use in the practice of this invention would be by way of test of the bacterial isolates from the plants or from various collections as to whether or not they fall within the category of ice nucleating or non-ice nucleating in accordance with the practice of this invention.

For this purpose, a test has been devised for identification of isolates as to whether they can be identified as having ice nucleating activity or as non-ice nucleating bacteria.

Isolates of bacteria were obtained from various sources. Some isolates were obtained from various collections throughout the country. Some 259 bacterial isolates were derived from various plants by the well known dilution plating technique.

Bacterial suspensions for testing for ice nucleating content were typically grown on a nutrient agar at 20° C. for 24 hours and suspended either in distilled water or 0.1 M phosphate buffer at pH 7.0. The nutrient agar was formulated of 3.3 g Bacto-Peptone, 2.7 g Difco nutrient broth, 25 ml glycerol and 2.0 yeast extract in 1 liter of distilled water with Bacto agar added in an amount of 15 g/l. The nutrient broth (NB) used in some experiments contained the ingredients listed above without the agar or glycerol.

Testing Bacterial Colonies for Ice Nucleation Activity at −5° C.

A −5° C. test surface was prepared by spraying aluminum foil with a 1% w/v solution of paraffin in xylene, removing the xylene in a 55° C. circulating oven, folding the foil into a flat-bottomed boat and floating the boat on a methanol-ethylene glycol-water solution maintained at −5° C. in a refrigerated constant temperature bath (P.M. Tamsen model M45 circulating water bath, P.M. Tamsen N.V., Holland). This bath was cooled with a Neslab model PBC-2 bath cooler (Neslab Instruments Inc., Portsmouth, N.H.). This refrigerated bath, when connected to an auxiliary insulated circulating bath, yielded a total −5° C. working surface of approximately 3000 cm². Within each bath, the temperature was regulated to about −5° C., with temperature differences between the two baths being less than 0.3° C. Care was required in placing the aluminum boats (ca. 500 cm² each) on the liquid surface to prevent entrapment of air bubbles between the aluminum and the liquid coolant. Discrete 2–6 day old colonies from agar plates were sampled with a sterile toothpick and the bacterial cells were suspended in approximately 0.1 ml of sterile distilled water to yield a turbid suspension (greater than $10^8$ cells/ml). Five 10 μl droplets of suspension from each colony were placed on the −5° C. test surface. A colony was considered to contain nuclei active at −5° C. if one or more of the five droplets froze within 30 seconds. This system was used for testing all isolates whether isolated from field samples or obtained from various culture collections, and all colonies selected for testing from dilution platings of washings from field samples.

259 Bacterial isolates were tested for ice nucleating activity at −5° C. with the following results:

TABLE

ACTIVITY OF ICE NUCLEATING ACTIVE BACTERIA AND NON-ICE NUCLEATING ACTIVE BACTERIA IN INCITING FROST DAMAGE TO SEEDLING CORN AT −5° C.

| Bacterial Species | Damage to treated corn plants at −4° to −5° C. | |
|---|---|---|
| | Damaged (signicantly greater than controls) | Undamaged (not significantly greater than controls) |
| | (Number of isolates) | |
| A. Isolates active as ice nuclei at −5° C. | | |
| *P. syringae* | 81 | 2 |
| *P. syringae*-like field isolates[a] | 28 | 0 |
| *P. coronafaciens* | 6 | 0 |
| *P. pisi* | 4 | 0 |
| *P. fluorescens* | 1 | 0 |
| *E. herbicola* | 2 | 0 |
| *E. herbicola*-like field isolates | 41 | 5 |
| Total ice nucleating active isolates tested | 163 | 7 |
| B. Isolates inactive as ice nuclei at −5° C. | | |
| *P. syringae* | 0 | 4 |
| *P. coronafaciens* | 0 | 1 |
| *P. glycinea* | 0 | 1 |
| *P. tabaci* | 0 | 3 |
| *P. phaseolicola* | 0 | 2 |
| *P. marginalis* | 0 | 1 |
| *P. fluorescens* | 0 | 2 |
| *P. aeruginosa* | 0 | 1 |
| *P. solanacearum* | 0 | 1 |
| *E. stewartii* | 0 | 4 |
| *E. carotovora* var *carotovora* | 0 | 2 |
| *E. chrysanthemi* | 0 | 2 |
| *E. herbicola* | 0 | 4 |
| *Escherichia coli* | 0 | 1 |
| *Xanthomonas campestris* | 0 | 2 |
| *Xanthomonas axonapodis* | 0 | 1 |
| *Corynebacterium nebraskensis* | 0 | 4 |
| Miscellaneous other isolates | 0 | 52 |
| Total non-ice nucleating active isolates tested | 0 | 89 |

Procedure for Testing Against Frost Damage

All 259 bacterial isolates were tested for their ability to incite frost injury to corn seedlings at −4° C. to −5° C. For this purpose seedling corn was sprayed with suspensions of $10^8$ cells/ml (ca. 0.5 ml/plant) in $PO_4$ buffer with the exception that 25 of the miscellaneous isolates tested were applied in nutrient broth. After inoculation, all plants were held in a mist chamber for 24 hours prior to exposure to freezing temperature (with the exception of 24 additional hours of incubation in ambient air in the cases of *E. herbicola*-like field isolates). It will be noted from the results tabulated above that none of the 89 bacteria tested as non-ice nucleating incited frost damage when added to the corn seedlings. On the other hand, 163 of the 170 bacteria tested as having ice nucleating activity caused frost damage when added to the corn seedlings. The seven that gave negative results may have had a very low fraction of cells active in ice nucleation or may not have successfully colonized corn leaves.

The effect of adding ice nucleating bacteria to other plants was also tested with wild plum and cherry blossoms. Frost damage to blossoms at −5° C. was examined in wild plum and cherry (*Prunus avium* L.), using dormant twigs containing flower buds collected during late February. The bases of the twigs were placed in water and the twigs were incubated in a controlled environmental chamber at 20° C. days and 12° C. nights with a 16 hour photoperiod and 60–80% relative humidity for approximately 28 days. When blossoms appeared, one half of the twigs were sprayed with suspensions of $10^7$ cells/ml of ice nucleating bacteria in nutrient broth while the other half was sprayed with nutrient broth alone. Both were incubated in a mist chamber for 24 hours prior to freezing at $-5°$ C. Blossoms of plum and cherry were without injury on plants sprayed with nutrient broth alone while the plants sprayed with ice nucleating bacteria were damaged. The opposite results could be achieved by treatment of the plants with non-ice nucleating bacteria. Thus, plants initially sprayed with ice nucleating bacteria would suffer injury while the plants also sprayed with non-ice nucleating bacteria in a nutrient broth would exhibit reduced damage. Similar protection can be obtained by the treatment of other plants, such as corn, beans, etc., with an inoculation of non-ice nucleating bacteria.

In the preferred practice of this invention, it is desirable to make use of non-ice nucleating bacteria that interfere with the growth of ice nucleating bacteria either by way of competing with the ice nucleating bacteria for sites which prevent establishment of the ice nucleating bacteria for growth and/or by way of being antagonistic, such as being destructive, of ice nucleating bacteria to prevent them from growing and/or interfering with their ability to initiate ice formation.

This is particularly significant when it is appreciated that ice formation can be nucleated by ice nucleating bacteria when present on the plant in sufficiently high concentration, even in the presence of increased amounts of non-ice nucleating bacteria. Thus, the application of interfering non-ice nucleating bacteria is desirable not only to adjust the balance in favor of the non-ice nucleating bacteria, but also to retard the growth of bacteria that nucleate ice or interfere with their ability to nucleate ice.

Application of such interfering non-ice nucleating bacteria is particularly effective when applied to the plants during an early stage of growth since then the non-ice nucleating bacteria can become well established on the plant while the plant is relatively free of bacteria, or at most, has a low population of bacteria, thereby to maintain the population of ice nucleating bacteria at a very low level, or, at best, practically non-existent throughout the life of the plant.

A test that has been used successfully to identify interfering non-ice nucleating bacteria comprises a practical test wherein isolates of non-ice nucleating bacteria are applied to leaves, such as leaves from a corn plant subsequently populated with the normal distribution of bacteria or inoculated with ice nucleating bacteria. Comparison is made with the leaves of the same plant that have not been pretreated with the isolate to determine the distribution in population of bacteria after a period of incubation.

By way of example of a laboratory technique for measurement of epiphytic bacterial populations, corn seedlings were inoculated with an isolate of non-ice nucleating bacteria, such as *E. herbicola*. Inoculated and non-inoculated plants were then sprayed with an isolate of ice-nucleating bacteria, such as *P. syringae* and then after an incubation period the inoculated and non-inoculated plants were homogenized for 30 seconds in 100 ml. of phosphate buffer at a pH of 7 in a high speed mixer.

Leaf homogenates were then plated on agar plates, using standard dilution plating procedures. The plates were incubated for 2 days at 28° C. Yellow colonies with raised centers, characteristic of *E. herbicola* and white colonies characteristic of *P. syringae* were counted to compare the number of colonies from the inoculated and non-inoculated leaves. When the number of yellow colonies from the inoculated plants is greater than the number of yellow colonies from the non-inoculated plants, or, more significantly, when the number of white colonies from the inoculated plants is reduced by comparison with the number of white colonies from the non-inoculated plants, the particular isolate can be identified as an interfering non-ice nucleating bacterium. Reduction in the number of white colonies is indicative of the fact that the isolate of the non-ice nucleating bacterium interfered with the ice nucleating bacterium by exhibiting an antagonism to such bacteria and/or competing with the growth of such bacteria.

In the examples heretofore described, the bacterial suspensions were applied to growth chamber grown seedlings having very low initial populations of bacterial epiphytes of unknown taxa on their leaves (usually less than 50–100 cells/gram fresh weight). Therefore, upon inoculation with bacterial suspensions, most of the bacteria present after inoculation were of the applied, bacterial species. The large bacterial populations arising on leaf surfaces due to bacterial growth during incubation would then be composed predominantly of the bacteria applied at inoculation.

Additions of *E. herbicola* var. ananus, (M232A), an interfering, non-ice nucleating bacterium, reduced frost damage when applied to plants treated with ice nucleating *P. syringae* as well as *E. herbicola* isolates. Plants were pretreated with $3 \times 10^8$ cells/ml M232A in nutrient broth and with nutrient broth alone prior to inoculation with a range of ice nucleating bacterium including *E. herbicola* (#26) and *P. syringae* isolate (#31). Frost damage to M232A pretreated plants was found greatly to be reduced at every cell density of #26 applied compared to control plants (M232A-26 v. nutrient broth (NB)-26 respectively). Frost damage to plants treated with a range of cell densities of *P. syringae* was also significantly reduced in the presence of M232A (M232A-31 v. NB-31), as indicated by the accompanying graph.

Ice nucleating active bacterial populations were reduced early in the growing season in the presence of M232A. Ice nucleation active bacteria apparently could not become established in significant numbers on plants already supporting substantial populations of antagonistic non-ice nucleating bacteria. The microbial ecology of the leaf surface appeared to be significantly changed, particularly early in the growing season, by the application of M232A in a nutrient solution. Total populations of bacteria and populations of bacteria resembling M232A on plants sprayed with nutrient broth were qualitatively and quantitatively indistinguishable from unsprayed plants at all sampling dates throughout the growing season.

It will be apparent from the foregoing that there is provided a method of reducing the proportion of ice nucleating active bacteria on leaf populations and thus frost injury by treatment of plants with interfering bacteria having no ice nucleation activity. Such bacteria readily colonized young plants and were effective in reducing ice nucleating active bacteria populations and frost injury especially when applied early in the growing season when it was best adapted for epiphytic growth on plant seedlings.

Due to the propagation of the bacteria, once the proportion has been changed by the addition of non-ice nucleating bacteria, the change in proportion will generally persist throughout the remainder of the life of the plant, or preferably deviate in favor of increasing population of non-ice nucleating bacteria, when application is made of interfering non-ice nucleating bacteria, so that only a single application of non-ice nucleating active bacteria would be required to yield reduction in frost injury of any subsequent date of freezing temperature. Since the change in proportion is of increasing significance during the early stages of plant growth, when the overall population of bacteria on the plant is less, it is desirable to make such application as early in the life of the plant as possible, although protection against frost damage will be observed by the treatment of the plants by adding non-ice nucleating bacteria at any stage of the plant life.

The amount of non-ice nucleating bacteria required to be added to get the desired protection against frost damage will depend greatly on the population of bacteria already present on the plant, with the amount increasing with the age of the plant for equivalent results.

The non-ice nucleating bacteria can be applied to the plants, in accordance with the practice of this invention, from aqueous medium with the application being most readily accomplished by suspending the bacteria cells in such medium and spraying the suspension on the plants. If desired, a nutrient, which will aid in proliferation of the bacterium on the plant after spraying, can be added to the suspension. It will be obvious that the concentration of cells in the suspension can vary. For example, it has been found that concentrations of from about $10^6$ to about $10^8$ cells/ml of the suspension are suitable to accomplish the ends of this invention. It is also obvious that the rate of application of the cell suspension will also vary depending upon the type of crop which it is desired to protect from freezing and the method by which it is applied, e.g. aerial or ground rig spraying. For example, protection of corn was afforded by spraying, from a ground operated spraying rig, a suspension of $10^7$–$10^8$ cells/ml in a nutrient broth one-half the strength of that described above at a rate of 100 gal./acre. In all cases, sufficient of the bacterium must be applied to achieve the freezing protection desired while the adverse economics of applying at too great a rate will obviously dictate the maximum rate of application.

The bacteria are generally of the rod-like type with flagellae which make it mobile. Thus they may be able to distribute themselves in a relatively short period of time, even though application may be made somewhat unevenly.

The importance of the rate of deposition for the amount of bacterium deposited on the plant is not significant since the bacterium propagates very rapidly, especially when deposited on the plants in nutrient media. In laboratory tests, the bacterium has been applied by liquid spray in which the bacteria are suspended in nutrient broth. It may be possible to dust lyophilized bacteria onto the plant as a powder, preferably with a powdered carrier as diluent and/or nutrient medium. Noticeable reduction in frost damage is achieved when the bacterium is applied in amounts of one-tenth the concentration described above while application can be made in concentrations greater than that described above although little, if any, additional benefit is derived by more than a ten-fold increase in such concentration.

For further examples of treatments of plants to reduce frost damage, reference can be made to the aforementioned U.S. Pat. No. 4,045,910.

In accordance with the theoretical concept of this invention, lowering of the temperature at which the plant freezes, with a corresponding reduction in frost damage, can be achieved by the treatment of the plants with non-ice nucleating bacteria, whereby the number of bacteria having ice nucleating activity is reduced with reference to that normally on the plants.

It will be understood that changes may be made in the details of formulation and operation without departing from the spirit of the invention, especially as defined in the following claims.

We claim:

1. The method for protecting plants against frost injury comprising treating the plants by the application of non-ice nucleating bacteria in an amount sufficient to increase the population prior to the onset of freezing temperature to increase the proportion of non-ice nucleating bacteria to ice nucleating bacteria from that normally present on the plants thereby to reduce the temperature at which frost injury occurs.

2. The method as claimed in claim 1 in which the non-ice nucleating bacteria applied to the plants are bacteria which interfere with the ice-nucleating bacteria.

3. The method as claimed in claim 2 in which the interfering non-ice nucleating bacteria are antagonistic to the ice nucleating bacteria.

4. The method as claimed in claim 2 in which the interfering non-ice nucleating bacteria interfere by occupying sites for growth of the ice nucleating bacteria.

5. The method as claimed in claim 1 in which the treatment to add the non-ice nucleating bacteria is made during an early stage of plant growth.

6. The method as claimed in claim 1 in which the treatment to apply the non-ice nucleating bacteria is made while the plant is in the seedling stage.

7. The method as claimed in claim 1 in which the bacteria are provided in an aqueous suspension and treatment is carried out by spraying the plants with the suspension.

8. The method as claimed in claim 1 in which the treatment of add the non-ice nucleating bacteria is made during the budding stage in the case of perennial plants.

9. A composition for topical application to plants for protection of the plants against frost injury comprising a carrier, and non-ice nucleating bacteria and a nutrient suitable for the bacteria admixed with the carrier, in which the non-ice nucleating bacteria are interfering bacteria which are antagonistic to or compete with ice nucleating bacteria.

10. A composition as claimed in claim 9 in which the non-ice nucleating bacteria are present in the suspension in an amount within the range of $10^6$–$10^8$ cells/ml.

11. A composition as claimed in claim 9 in which the carrier is water in which the non-ice nucleating bacteria are suspended.

* * * * *

UNITED STATES PATENT OFFICE
CERTIFICATE OF CORRECTION

Patent No. 4,161,084            Dated July 17, 1979

Inventor(s) Deane C. Arny and Steven E. Lindow

It is certified that error appears in the above-identified patent and that said Letters Patent are hereby corrected as shown below:

page 1, before the first paragraph, insert the following paragraph:

-- The invention described herein was made in the course of work under a grant or award from the Department of Health, Education and Welfare. --

Signed and Sealed this

Twenty-ninth Day of January 1980

[SEAL]

Attest:

SIDNEY A. DIAMOND

Attesting Officer       Commissioner of Patents and Trademarks